(12) United States Patent
Kalamas

(10) Patent No.: US 8,571,890 B2
(45) Date of Patent: *Oct. 29, 2013

(54) SYSTEM AND METHOD FOR GENERATING A MEDICAL HISTORY

(75) Inventor: Alicia Gruber Kalamas, Piedmont, CA (US)

(73) Assignee: MedSleuth, Inc., San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/453,389

(22) Filed: Apr. 23, 2012

(65) Prior Publication Data

US 2012/0203574 A1 Aug. 9, 2012

Related U.S. Application Data

(63) Continuation of application No. 13/043,909, filed on Mar. 9, 2011, now Pat. No. 8,165,898, which is a continuation of application No. 12/259,273, filed on Oct. 27, 2008, now Pat. No. 7,908,154.

(51) Int. Cl.
*G06Q 10/00* (2012.01)
*G06Q 50/00* (2012.01)

(52) U.S. Cl.
USPC .................................................. 705/2; 705/3

(58) Field of Classification Search
USPC ........................................................ 705/2–3
See application file for complete search history.

(56) References Cited

U.S. PATENT DOCUMENTS

| 3,566,370 A | 2/1971 | Worthington, Jr. et al. |
| 4,130,881 A | 12/1978 | Haessler et al. |
| 4,731,725 A | 3/1988 | Suto et al. |
| 4,872,122 A | 10/1989 | Altschuler et al. |

(Continued)

FOREIGN PATENT DOCUMENTS

| EP | 608593 | 8/1994 |
| EP | 1327948 | 7/2003 |
| JP | 2003-162859 | 6/2003 |
| KR | 10-20010098318 | 11/2001 |

OTHER PUBLICATIONS

Bader, Angela M., Computer-Based Preoperative Assessment, International Anesthesiology Clinics, Spring 2002, c.40(2), pp. 193-199.

(Continued)

*Primary Examiner* — Joseph Burgess
(74) *Attorney, Agent, or Firm* — Donald L. Bartels; Bartels Law Group

(57) ABSTRACT

A system and method for generating a medical history that is determined based on the patient's medication list. Medications are taken for specific indications, i.e., disease and/or symptom, and the system includes a knowledge base of all known medications and associated indications. Preferably, an expert system allows the patient, nurse or other user, to enter all or part of the name of the patient's medications, and creates a list of probable medications by determining which of the known medications the patient most likely takes. Based on a user selected probable medication, the system creates a list of probable medical indications associated with the selected medication. Based on a user selected probable indication, the system generates a medical history for the patient. The probable medications and probable medical indications are determined preferably based on the patient's demographic data, historical data for other patients, and responses to follow-up questions generated by the system.

24 Claims, 3 Drawing Sheets

(56) References Cited

U.S. PATENT DOCUMENTS

| | | | |
|---|---|---|---|
| 5,025,374 | A | 6/1991 | Roizen et al. |
| 5,517,405 | A | 5/1996 | McAndrew et al. |
| 5,574,828 | A | 11/1996 | Hayward et al. |
| 5,897,493 | A | 4/1999 | Brown |
| 5,937,387 | A | 8/1999 | Summerell et al. |
| 6,003,020 | A | 12/1999 | Hazlehurst et al. |
| 6,334,192 | B1 | 12/2001 | Karpf |
| 6,658,396 | B1 | 12/2003 | Tang et al. |
| 6,826,536 | B1 | 11/2004 | Forman |
| 6,968,375 | B1 | 11/2005 | Brown |
| 7,252,636 | B2 | 8/2007 | Brown |
| 7,290,016 | B2 | 10/2007 | Byers |
| 7,624,029 | B1 * | 11/2009 | Ghouri .............. 705/3 |
| 2001/0053875 | A1 | 12/2001 | Iliff |
| 2002/0002472 | A1 | 1/2002 | Abraham-Fuchs |
| 2002/0022975 | A1 | 2/2002 | Blasingame et al. |
| 2002/0023144 | A1 | 2/2002 | Linyard et al. |
| 2002/0029157 | A1 * | 3/2002 | Marchosky .............. 705/3 |
| 2002/0091546 | A1 | 7/2002 | Christakis et al. |
| 2003/0065241 | A1 | 4/2003 | Hohnloser |
| 2003/0158755 | A1 | 8/2003 | Neuman |
| 2003/0204415 | A1 | 10/2003 | Knowlton |
| 2003/0208382 | A1 * | 11/2003 | Westfall .............. 705/3 |
| 2004/0122706 | A1 | 6/2004 | Walker et al. |
| 2004/0199332 | A1 | 10/2004 | Iliff |
| 2005/0197865 | A1 | 9/2005 | Jordan |
| 2005/0273359 | A1 | 12/2005 | Young |
| 2008/0059403 | A1 | 3/2008 | Byers |
| 2008/0081955 | A1 * | 4/2008 | Eisenhandler et al. ....... 600/300 |

OTHER PUBLICATIONS

Parker, Brian M., et al., Redefining the Preoperative Evaluation Process and the role of the Anesthesiologist, Journal of Clinical Anesthesia, 2000, pp. 350-356.

Phillips, Chester, Pre-Anesthesia Evaluation & Data Capture, Anesthesia Patient Safety Foundation Newsletter, Summer 2001, v. 16 (2), no page numbers.

* cited by examiner

SYSTEM AND METHOD FOR GENERATING A MEDICAL HISTORY

CROSS-REFERENCE TO RELATED APPLICATIONS

This application is a continuation of U.S. application Ser. No. 13/043,909, filed Mar. 9, 2011, now U.S. Pat. No. 8,165,898, which is a continuation of U.S. application Ser. No. 12/259,273, filed Oct. 27, 2008, now U.S. Pat. No. 7,908,154.

FIELD

This invention relates to medical histories, and more specifically, relates to generating a medical history.

BACKGROUND

A detailed medical history is the cornerstone for accurate patient assessments and medical diagnosis. Traditional history taking by clinicians is often incomplete and time consuming because it requires not only collecting the information, but also accurately documenting it. Clinicians are typically highly paid medical professionals. A need exists, therefore, for a system that can take an accurate and complete medical history without the direct participation of costly medical personnel.

Computerized systems are available for patients to enter medical data themselves in response to queries. Typically, these systems use a predetermined set of questions for the patient, or another user on behalf of the patient, to answer. These computerized systems are considered superior to traditional history taking techniques because typically such systems 1) are highly structured to include all pertinent questions and never forget to ask a question; 2) can be done at the patient's pace at a time and place that is convenient for the patient; 3) elicit sensitive information that is often underreported in the face-to-face interview; 4) can be administered in different languages; 5) prepare patients for the subsequent encounter with the clinician; 6) can calculate scores to clinical rating scales for easy interpretation by a physician; and 7) provide legible summaries that can be manipulated by or directly entered into an electronic medical record.

A known automated computer-based medical history taking system is described in U.S. Pat. No. 3,566,370 which provides for the development of and printout of a patient's medical history. The system includes a display for presenting questions with multiple choice answers to a patient. Subsequent questions are presented to the patient in accordance with the answers to previous questions. Therefore, medically related questions are automatically propounded according to U.S. Pat. No. 3,566,370, even though not specifically selected for review by a patient.

Similarly, U.S. Pat. No. 7,290,016 describes a system and method for generating and storing a medical history that uses a questionnaire database in which answers to questions are correlated with subsequent questions. The questionnaire database includes a plurality of questions and corresponding multiple choice responses. The responses are associated with additional questions in the questionnaire database. Therefore, the pattern through the questionnaire database is not predetermined according to U.S. Pat. No. 7,290,016, but is dependent upon the pattern of answers.

While both of the above-mentioned systems and methods for eliciting a medical history are superior to traditional history taking techniques, i.e., by a clinician or paper questionnaire, these and other known systems and methods still have serious drawbacks that limit their effectiveness and have hindered their widespread acceptance by both patients and the medical community at large.

First, these known computer based questionnaires contain too many questions, many of which are not relevant to the patient being asked the question, i.e., many questions are not patient specific. While known systems do employ branch-chain logic to hone in on specific patient complaints and clarify symptoms, these systems have no way of identifying which questions are the most important to ask the patient upfront. As such, these known systems require the patients to answer too many irrelevant questions. Furthermore, patients make inadvertent errors during standard computer interviews of these known systems because the patients misunderstand the questions, forget, and/or become tired and careless. Studies such as noted by Carr have found that these drawbacks lead to an error rate in patient directed computer interviews of 3%-7%.

There is a need, therefore, for a patient-driven computer based system that is not only highly patient specific, but also provides a "checks and balance" system for the patient to help eliminate some of the errors that occur from patients misunderstanding questions and/or forgetting or inadvertently misrepresenting certain components of their medical history. There is also a need for the system to learn from both the patient's particular situation and from the system's experience with prior users in order to provide more, relevant questions to the patient in order to more readily obtain a more accurate medical history from the patient.

SUMMARY

The system and method according to certain embodiments of the present invention substantially overcome the deficiencies of known systems and methods by generating a medical history from the medications the patient is taking. A preferred embodiment comprises utilizing an expert system and machine learning to generate a medical history for a patient from the medications the patient is taking.

These and other embodiments, features, aspects, and advantages of the invention will become better understood with reference to the following description, appended claims and accompanying drawings.

Reference symbols or names are used in the Figures to indicate certain components, aspects or features shown therein, with reference symbols common to more than one Figure indicating like components, aspects or features shown therein.

DETAILED DESCRIPTION

The system and method according to certain embodiments of the present invention is preferably implemented in a computer device. Any type of general purpose computer comprising one or more computers can be used. The computer may be a device, including but not limited to, a personal computer, personal digital assistant (PDA), cellular phone, or the like. Alternatively, the system could be implemented on a special purpose computer or a computer network specifically created to perform the functions of the present invention. Alternatively, the system could be implemented on a server system connected to a wide area network accessible from any location connected to the network. According to another alternative, certain embodiments of the invention may be used in conjunction with a call center, for example, wherein a person is prompted by their computer device to ask questions of the patient or other user, the computer device being operable to implement certain embodiments of the invention.

Figure 3:
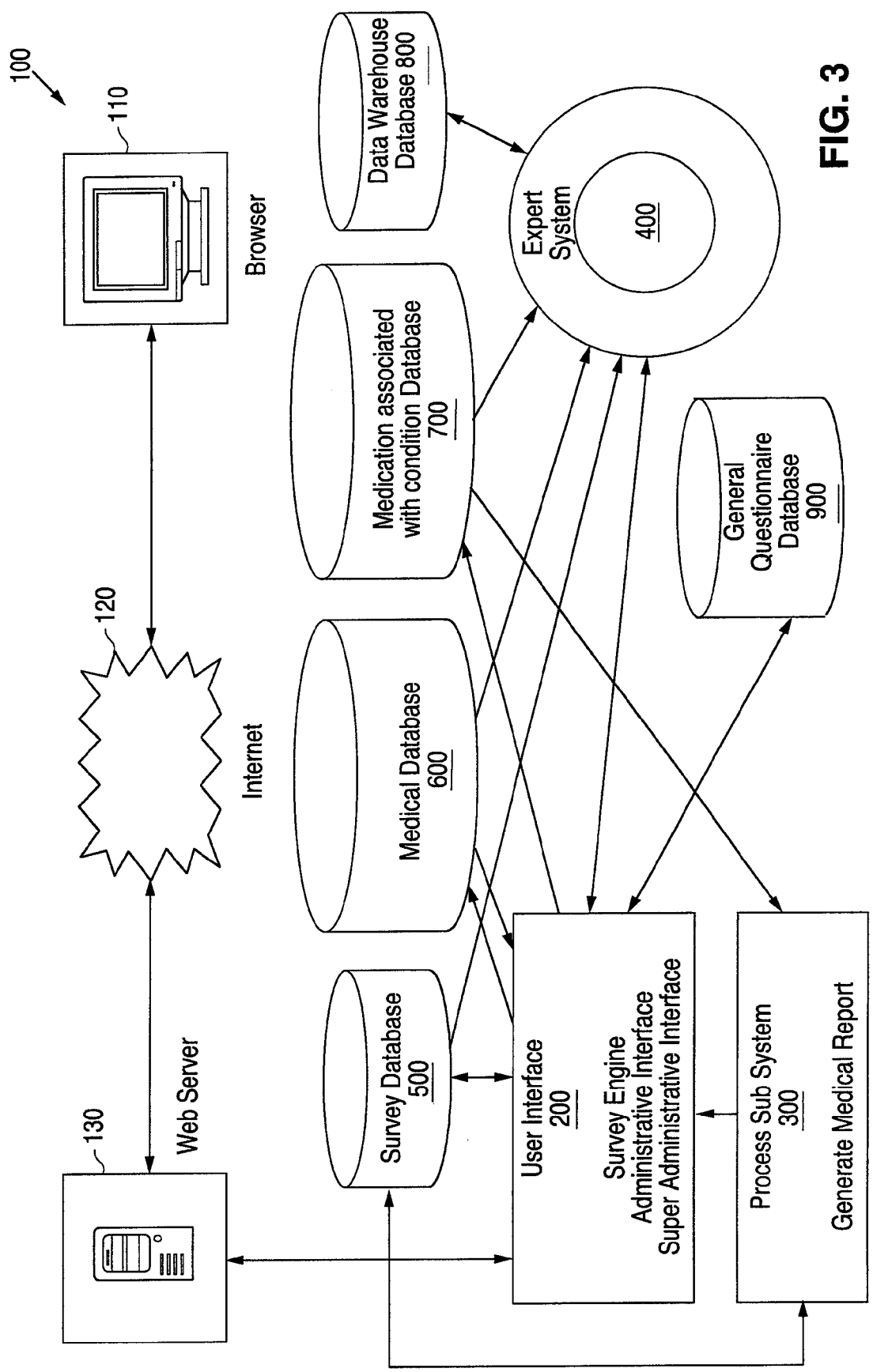
FIG. 3 illustrates a block diagram of a system according to certain embodiments of the present invention.

FIG. 3 is a block diagram of the System 100 implemented in accordance with certain embodiments of the invention. System 100 includes User Interface 200, Processing Subsystem 300, Expert System 400 and several databases 500-900.

User Interface 200 is preferably a browser-based application that works with Processing Subsystem 300 and Expert System 400 to perform the various functions of System 100 for creation and retrieval of medical histories. Preferably, the user (not shown) may use any suitable browser 110 to access the User Interface 200 via the Internet 120 and a Web Server 130, as illustrated in FIG. 3.

Expert System 400 is at the core of System 100. An expert system, broadly defined, is a software system that attempts to reproduce the performance of one or more human experts by analyzing information, usually supplied by the user of the system, and utilizing what appears to be reasoning capabilities. Machine learning is concerned with the design and development of algorithms and techniques that allow computers to learn from either inductive or deductive reasoning. The Expert System 400 in the exemplary System 100 according to the embodiment in FIG. 3 generates successive survey questions whereby those questions are informed via several inputs. Initially, those inputs are patient self-reported medications and, preferably, patient demographics. Based on those initial inputs, Expert System 400 preferably draws upon several databases in an iterative fashion: 1/Medication Database 600 that lists the correct spelling of all known medications, both branded, generic, and homeopathic (e.g. herbal medications); 2/Medication associated with Condition Database 700, also referred to as "Medication/Condition Database" 700, that links each of these medications to their indicated uses for all known relevant medical conditions and/or disease symptoms; both approved and not approved by the Federal Drug Administration (FDA) or similar global regulatory bodies; and 3/Data Warehouse Database 800 which is populated with data from patients who have previously used the system.

The process of formulating a medical history using System 100 can be initiated in one of several ways. According to one embodiment, a customer-user, e.g., clinician or hospital administrator, accesses the System 100 via the User Interface 200 and enters a patient's demographics, e.g., age, gender, weight, vital signs, and assigns the patient a password. This demographics and password data is used to initiate the creation of a survey. Patient demographics are preferably stored in an anonymous fashion in the Survey Database 500; alternatively, demographics data including patient specific data is stored in the Survey Database 500.

Figure 2:
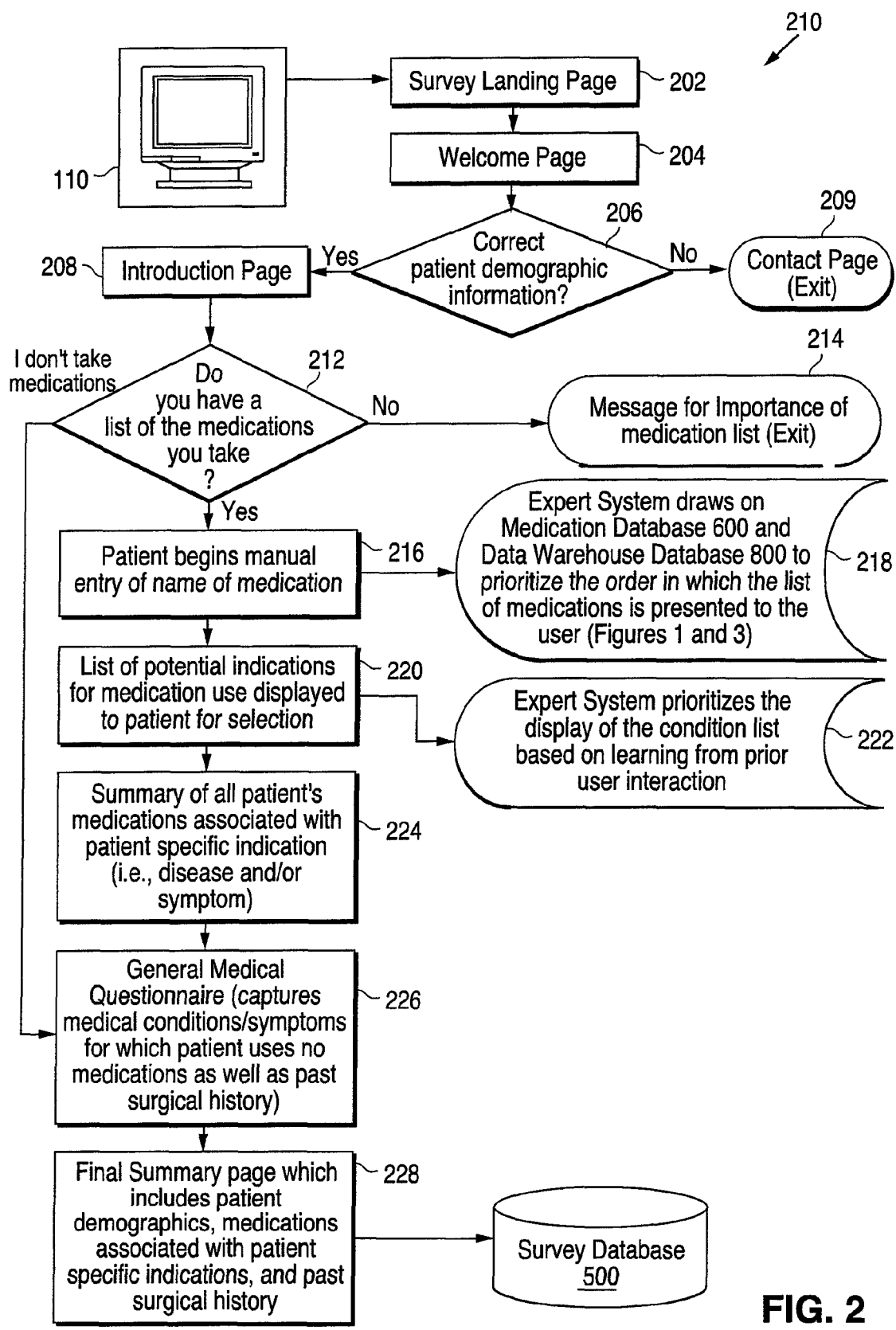
FIG. 2 illustrates a survey flowchart powered by the survey engine according to an exemplary embodiment of the present invention.

FIG. 2 illustrates a survey flowchart 210 powered by the survey engine according to an exemplary embodiment of the present invention. The patient or other user of the system can access the System 100 via the User Interface 200 through entry of a Uniform Resource Locator (URL) preferably via a suitable browser application 110, seen in FIGS. 2 and 3, operating on a computer device. In response to entry of the URL, the browser application 110 directs the user to a survey landing page 212 where the user is prompted for entry of their pre-assigned password. Alternatively, a dedicated data entry terminal may be used to access to the System 100 via the User Interface 200 and enter the pre-assigned password. In response to entry of the pre-assigned password, the system preferably enables the user to have access to an initial survey page, i.e., a "Welcome Page" 204 shown in the example in FIG. 2.

From the Welcome page 204 in the example in FIG. 2, the patient or other user of the system is asked at 206 to confirm that the patient demographic data is correct. The process proceeds to an Introduction Page 208 if the demographic data is confirmed; otherwise the process proceeds to a Contact Page (Exit) 209; and exits the process 210 to request the user to enter the correct demographic information.

After the Introduction Page 208 is displayed to the user, at 212, the user is asked if the user has a list of medications the patient takes, i.e., medications used by the patient. A message regarding the importance of providing a medication list at 214 is displayed if the user indicates he/she doesn't have the list, and the process 210 is exited. Alternatively, if the user indicates in response to the question at 212, that the patient doesn't take medications, e.g., "I don't take medications", the process 210 proceeds to 226 in FIG. 2.

In response to the user indicating at 212 that they have a list of the medications taken, the system enables the patient to begin manual entry of name(s) of medication(s) at 216. The user is prompted to enter all or part of the names of the medications used by the patient.

Figure 1:
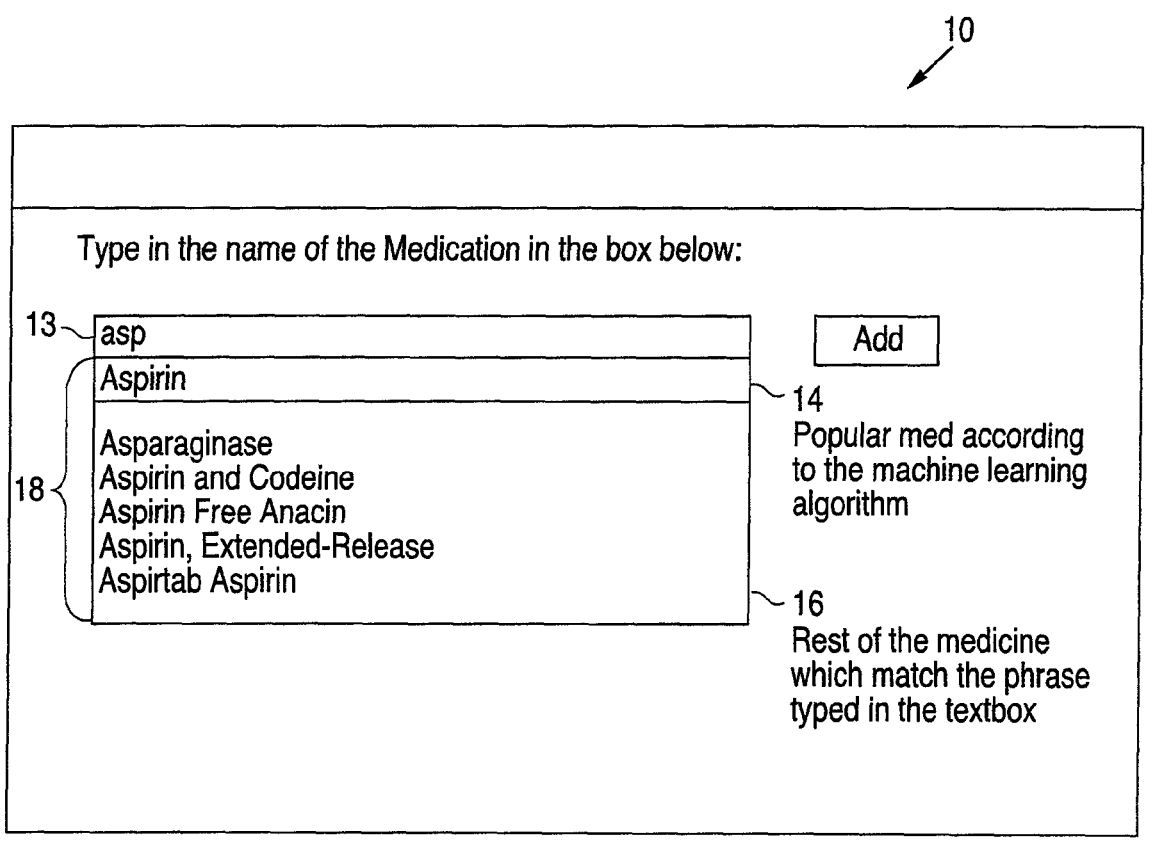
FIG. 1 illustrates an exemplary display regarding a survey question regarding medications according to an embodiment of the present invention.

FIG. 1 illustrates an exemplary display 10 regarding a survey question regarding medications according to an embodiment of the present invention. According to one aspect of certain embodiments of the invention, a user enters the first few letters of the name of one of the medications used by the patient. The user is referred to herein variously as the "patient" or "user", however, it should be appreciated that the user may be the patient, a healthcare provider, or another authorized person using the system on behalf of the patient.

Preferably, a text box 13 is provided to display the letters typed by the user for the medication name. If the letters entered by the user are not recognized by the system as any known medication, the system preferably asks the user to recheck the spelling on their pill bottle or prescription, and reenter letters in the name.

As shown in the example in FIG. 1, based on the letters entered by the user for the medication, a drop down function appears with a much abbreviated medication list. A two-tiered drop down list 18 in FIG. 1 is displayed in response to entry of a portion of the name, i.e., "asp". Referring to FIGS. 1-3, this list 18 is generated by the survey engine in User Interface 200 by integrating information from the Expert System 400 and the Medication Database 600. The order in which this list is presented to the user is not strictly alphabetized, instead, the order in the list is prioritized as described further below.

As shown at 218 in the exemplary embodiment in FIG. 2, the Expert System 400 cross-references the Medication Database 600 and the Data Warehouse Database 800 for prioritizing the order in which the list of medications is presented to the user. According to certain embodiments, the Expert System 400 provides the "first-tier" 14 of medications by generating its "best guess", according to a machine learning algorithm, by comparing the demographic data from the current user to historical data from matched controls preferably stored in the Data Warehouse Database 800. The historical data is from other users of the method and for other patients, or from prior uses by the user or for the patient. Matched controls refers to the historical data accumulated by the system matching the user in some way, including but not limited to, matching based on one or more of the age, gender, race, or other portion of the demographic data. For example, as shown in FIG. 1, the user entered "asp" as one of the patient's medications. If 100 patients entered "asp" into the system and 99 of these patients said they take Aspirin and only 1 said they take Aspartate, the system "learns" from this previous data in order to "know" that when a patient enters "Asp", they likely take Aspirin, not Aspartate. Therefore, based on limited input from a patient, the system and method according to a preferred embodiment uses historical data and the process of machine learning to formulate the drop down list for the patient which prioritizes those medications in the list which are most likely to be taken by a given patient. The prioritized list is ordered from most likely to least likely, as its first "best guess" of the likely medication to which the patient is referring. Certain embodiments also include integrating data stored in the repository from prior users, e.g., historical data on patient's, age, and gender, to further speciate the medication list. In addition, other patterns of matched controls, aside from age, gender, and race, may emerge in the historical data acquired using the system, that may be useful in comparison and generation of the best guess.

A tier "two", identified as 16 in FIG. 1, in the prioritized list 18 contains other likely medications, other than the first tier best guess of the likely medication, that match the phrase typed in by the user in the text box 13 and is provided from the Medication Database 600.

The user is preferably prompted to select the medication used by the patient from the two-tiered list 18. At 220 in FIG. 2, in response to the user selection, a prioritized list of potential indications associated with use of the selected medication is displayed to the patient, or other user, for selection, as explained in further detail below. Indications as used herein refer to disease states and/or symptoms associated with a medication. The system and method according to embodiments of the present invention enables the patient to select their specific medical conditions from this prioritized list; thus enabling the patients to easily reconcile their medications with their associated disease states and/or symptoms.

Since medications are used for specific indications, the system 100 includes Medication associated with Condition Database 700 that links all known medications to their respective indicated uses for all known relevant medical conditions and/or disease symptoms; thus all known medications are associated with known specific indications for which the medication may be used.

In response to the patient selecting their medication from the list of medications, at 220, the system presents the patient with a list of plausible medical indications, ordered from most to least likely, as its first "best guess" of the likely indications, e.g., conditions, disease and or symptom, for which the patient is using the medications. The prioritized list of diseases and/or symptoms from the expert system is preferably presented to the patient using lay person terminology.

For 220, the Expert System 400 preferably draws on the Survey Database 500, the Medication/Condition Database 700, and the Data Warehouse Database 800 to formulate the list of potential indications for which the patient may use the selected medication. As shown at 222 in the example in FIG. 2, the Expert System 400 prioritizes the display of the list of indications, also referred to herein as "conditions", presented to the user. As shown at 222, the order in which this list of indications is presented to the user is highly patient specific as it is based, at least in part, on learning from prior users' interactions, according to a preferred embodiment. The order according to the preferred embodiment is selected by Expert System 400 based on demographic data from the current user in Survey Database 500, historical data from matched controls from Data Warehouse Database 800, and a comprehensive Medication/Condition database which has all medications associated with their known indications.

Preferably, the Expert System 400 refines its "best guess" through sequential questions to the patient until both the user and the system are satisfied that current medications, as well as associated medical conditions, have been correctly identified. According to an exemplary embodiment, in response to a patient entering "Motrin" as one their medications, for example, the system and method automatically follows up with the question, "Do you take Motrin for A) Fever B) Pain C) Headaches D) Toothache or E) Arthritis?". Depending on the patient's response, further follow-up questions may be presented to the user. For example, if a patient answers "B", certain embodiments will follow up with a question asking the patient to specifically locate and describe their pain. In this way, certain embodiments automatically prompt the patient/user to reconcile their medications with their disease states and/or symptoms and also provide a pathway for getting greater specificity about the answers to the questions.

Information associated with the refined "best guess" is stored within the Data Warehouse 800 as an incremental data point to help the system "learn" and improve its predictive power for each subsequent patient assessment, i.e., it uses a process known as "machine learning". Additionally, each individual patient's results, i.e., survey, are aggregated with his/her demographic data in a standard format to create a complete medical history which can then be shared back with the patient's clinical representative and used as input into the clinical decision making process for the patient's care.

According to another aspect of certain embodiments of the invention, the system integrates data stored in the repository from prior users to prioritize which disease states are most relevant for that particular patient. For example, if the system knows the user who indicated taking Motrin is a 50 year old male scheduled for a knee replacement surgery, it has a knowledge base from inputs from other prior patients in order to enable the system to suggest that this patient most likely takes Motrin for pain and arthritis. Thus, in response to this particular patient entering "Motrin" as one of their medications, certain embodiments of the system automatically ask the user, "Do you take Motrin to control the pain from arthritis?" as opposed to presenting the complete list of indications. In essence, the system utilizes what appears to be reasoning capabilities to reach conclusions. In this case, the data available, i.e., 50 year old man scheduled for a knee replacement, determines which inference rules will be used, i.e., it is a data driven system.

According to an aspect of preferred embodiments of the invention, the sequence of steps taken to formulate additional questions for an individual user is dynamically synthesized with each new user. That is, the system preferably is not explicitly programmed when the system is built, but rather formulates questions based on the current information provided about the specific patient, e.g., age, gender, chief complaint, etc., and historical data from matched controls.

According to an aspect of certain embodiments of the invention, the deducing of a patient's medical history is accomplished by an expert system by applying specific historical knowledge, rather than a specific technique. Thus, if the expert system does not produce the desired result, i.e., asks the patient if they take Motrin for the pain of arthritis, but the patient really takes it for headaches, the expert system has the ability to expand its knowledge base. Thus, if the system according to certain embodiments interviews 100 patients for knee replacement surgery, for example, and 75 take Motrin for pain and 25 take Motrin for headaches, it synthesizes this knowledge into its database; the more data the system accrues, the smarter and more accurate it becomes at deducing medical histories of future users.

From the ordered list of indications, the system enables the user to select the indication for which the patient uses their medication. This allows the user to quickly and easily reconcile the patient's medications with the patient's associated conditions. In response to the reconciliation, the system and method can move forward with the automated creation of a medical history for the patient.

At 224 in FIG. 2, a summary is generated of all the patient's medications associated with patient specific indication, i.e., disease and/or symptoms. Preferably, the summary is displayed to the user.

Since patients have medical conditions for which they may not take any medications, e.g. heartburn, mitral valve prolapse, seasonal allergies, a General Questionnaire Database 900, illustrated schematically in FIG. 3, contains additional questions to ensure the medical history recorded by System 100 is comprehensive. The user is preferably presented, at 226, with a General Medical Questionnaire for capturing medical conditions/symptoms for which patient uses no medications as well as past surgical history.

In the example in FIG. 2, at 228, the user is presented with a final summary page which includes, in this example, patient demographics, medications associated with patient specific indications, and past surgical history. A summary of other information, preferably including medical conditions/symptoms for which patient uses no medications is also included in the final summary page which is preferably stored in the survey database 500.

All data from the survey completed by the user is preferably sent to Processing Subsystem 300, illustrated in FIG. 3. The system is preferably pre-programmed with all layperson's terms associated with widely accepted medical terminology so that, in conjunction with the patient completing the questionnaire, the system preferably generates a medical history using the widely accepted medical terminology. The Processing Subsystem 300 converts any remaining layperson terminology back to the widely accepted medical terminology, if available, using the information pre-programmed within the Medication/Condition Database 700. Therefore, when Processing Subsystem 300 generates the medical history for an official medical record, the disease states preferably appear using widely accepted medical terminology, not layperson terminology. For example, if the patient selects the layperson's term "Cold Sore", the system preferably uses the term "Herpes Labialis" in generating the medical history.

The system and method preferably enables the medical history generated by the expert system to be easily viewed on a network with password access or to be directly entered into an electronic medical record.

Having disclosed exemplary embodiments, modifications and variations may be made to the disclosed embodiments while remaining within the scope of the invention as described by the following claims.

What is claimed is:

1. A method for generating a medical history for a patient, comprising:
   obtaining from a user at least a portion of the names of each of the medications the patient is taking;
   obtaining demographic data for the patient and historical data for other users of the method;
   creating a list of probable medications using a computer processor, including determining which known medications are the probable medications that are more likely taken by the patient based on the at least a portion of the medication name received from the user, based on the patient's demographic data and the historical data, and based on a first knowledge base of medications,
   causing the list of probable medications to be displayed to the user; and
   receiving a selection from the user of one of the probable medications on the list of probable medications;
   for each one of the selected probable medications:
      (i) creating a list of probable medical indications associated with the respective medication using a computer processor, wherein the probable medical indications are diseases or symptoms, including determining which known medical indications are probable medical indications for which the patient most likely takes the identified medication based on the patient's demographic data and the historical data, and based on a second knowledge base of known medical indications for the respective medication;
      (ii) causing the list of medical indications to be displayed to the user; and
      (iii) receiving a selection from the user of one or more of the probable medical indications on the list; and
   generating a medical history for the patient based on the user selected probable medical indications and respective medications.

2. The method of claim 1, wherein the historical data from other users of the method comprises data for other patients who match at least a portion of the demographic data of the patient.

3. The method of claim 1, further comprising ordering the list of probable medications starting with the known medications most likely taken by the patient.

4. The method of claim 1, wherein the list of probable medical indications is ordered from the most likely probable medical indications sequentially followed by less likely probable medical indications, with the most likely probable medical indications displayed at the top of the list.

5. A method for generating a medical history for a patient, comprising:
   obtaining from a user at least a portion of the names of each of the medications the patient is taking;
   obtaining historical data for other patients who have used the method;
   creating a list of probable medications using a computer processor, including determining which known medications are the probable medications that are more likely taken by the patient based on the at least a portion of the medication name received from the user, based on the historical data, and based on a first knowledge base of medications,
   causing the list of probable medications to be displayed to the user; and
   receiving a selection from the user of one of the probable medications on the list of probable medications;
   for each one of the selected probable medications:
      (i) creating a list of probable medical indications associated with the respective medication using a computer processor, wherein the probable medical indications are diseases or symptoms, including determining which known medical indications are probable medical indications for which the patient most likely takes the identified medication based on the historical data, and based on a second knowledge base of known medical indications for the respective medication;

(ii) causing the list of medical indications to be displayed to the user; and (iii) receiving a selection from the user of one or more of the probable medical indications on the list; and generating a medical history for the patient based on the user selected probable medical indications and respective medications.

6. The method of claim 5, wherein the historical data comprises historical data for other patients who match at least a portion of the demographic data of the patient.

7. The method of claim 5, further comprising:
selectively for each one of the selected probable medications, causing a question to be generated and to be displayed to the user, wherein the question is based at least on the selected probable medication, demographic data for the patient, and historical data for other patients from other users of the method.

8. The method of claim 7, wherein the list of probable medical indications displayed to the user includes ordering of the probable medical indications on the list based on a response received from the user to the question.

9. The method of claim 5, further comprising dynamically generating questions in response to previous responses received from the user, to generate additional information for inclusion in the patient's medical history.

10. The method of claim 1, wherein the determining is further based on historical data for the patient.

11. The method of claim 5, wherein the user selected probable medical indications and respective medications are provided in the medical history using widely accepted medical terminology.

12. The method of claim 1, wherein the historical data from other users of the method includes inputs provided using the method.

13. The method of claim 1, wherein the demographic data includes at least one of the patient's age, gender, diseases, and symptoms.

14. The method of claim 5, wherein the list of medical indications is presented to the user using lay person terminology.

15. The method of claim 5, wherein the at least a portion of the name of the medication used by the patient comprises at least the first two letters of the name.

16. The method of claim 5, further comprising enabling secure viewing of the generated medical history via a network using password access.

17. The method of claim 1, further comprising entering the generated medical history into an electronic medical record.

18. The method of claim 5, wherein the medical history is generated via an expert system and machine learning.

19. The method of claim 5, further comprising
presenting one or more questions to the user regarding medical conditions, symptoms, and past surgical history for the patient for which the patient uses no medications; and
wherein the medical history includes information based on user responses to the one or more questions.

20. The method of claim 5, wherein the step of obtaining from a user an identification of each of the medications the patient is taking comprises receiving input from the user of at least a portion of the name of each of the medications the patient is taking, and wherein the step of creating a list of probable medications further includes determining which known medications are the probable medications that are more likely taken by the patient based on the at least a portion of the medication name received from the user.

21. A system for generating an automated medical history of a patient, comprising:
a user interface for receiving from the user at least a portion of the names of each of the medications;
a first computer database for storing a library of known medications and their respective medical indications;
a second computer database for storing demographic data for the patient and a third database for storing historical data of other patients obtained through prior uses of the system;
a computer implemented expert system for creating a list of probable medications based on a determination of which known medications are probable medications based on the at least a portion of the medication name received from the user, based on the patient's demographic data stored in the second database and the historical data stored in the third database, and based on the known medications in the first database;
wherein the user interface is further for causing the list of probable medications to be displayed to the user, and for receiving selection from the user of one of the probable medications from the list of probable medications; the expert system is further for creating a list of probable medical indications associated with the selected probable medication based on a determination of which known medical indications are probable medical indications for which the patient most likely takes the selected medication using the known medications and their respective medical indications stored in the first database and based on the patient's demographic data stored in the second database and the historical data stored in the third database;
the user interface is further for causing the list of probable medical indications to be displayed to the user and for receiving selection from the user one or more of the probable medical indications on the list of probable medical indications; and
wherein the expert system operative to generate a medical history for the patient that includes at least the selected probable medication and the selected one or more probable medical indications.

22. The system of claim 21, further comprising a fourth computer database for storing questions for capturing medical conditions, symptoms, and past surgical history for the patient for which the patient uses no medications, said user interface is further for causing the questions to be displayed to the user and for receiving the answers to these questions.

23. The system of claim 21, wherein the expert system is further for facilitating the input of information from the user via the user interface by dynamically generating additional questions in response to previous responses provided by the user.

24. The system of claim 21, wherein the expert system includes machine learning capabilities.

* * * * *